(12) United States Patent
Guillo et al.

(10) Patent No.: US 9,603,747 B2
(45) Date of Patent: Mar. 28, 2017

(54) ADHESIVE TAPE MADE OF SILICONE INTENDED FOR MEDICAL APPLICATIONS

(71) Applicant: ZODIAC AUTOMOTIVE DIVISION, Plaisir (FR)

(72) Inventors: Jean-Roger Guillo, Serezin de la Tour (FR); Jean-Francois Lecoeuvre, Sorbiers (FR); Melanie Guillermin, Lyons (FR)

(73) Assignee: ZODIAC COATING (FR)

( * ) Notice: Subject to any disclaimer, the term of this patent is extended or adjusted under 35 U.S.C. 154(b) by 966 days.

(21) Appl. No.: 13/911,250

(22) Filed: Jun. 6, 2013

(65) Prior Publication Data

US 2014/0134375 A1    May 15, 2014

Related U.S. Application Data

(60) Provisional application No. 61/725,681, filed on Nov. 13, 2012.

(51) Int. Cl.
*A61F 13/02* (2006.01)
*A61L 15/26* (2006.01)
(Continued)

(52) U.S. Cl.
CPC ...... *A61F 13/0253* (2013.01); *A61F 13/0256* (2013.01); *A61F 13/0269* (2013.01);
(Continued)

(58) Field of Classification Search
CPC ........ C09J 183/08; C09J 183/06; C09J 7/045; A61F 13/0253; A61F 13/0256; A61F 13/0269; A61L 15/26; A61L 15/28; A61L 15/52; A61L 15/58; B32B 27/12; B32B 5/022; B32B 7/12; B32B 3/266; B32B 2535/00; B32B 2405/00; B32B 2307/7265; B32B 2307/724; B32B 2307/4026; B32B 2262/062; B32B 2262/0284; C08L 83/04; C08L 83/08; C08L 27/12; C08L 67/02; C08L 1/00; C08G 77/04; C08G 77/24; Y10T 428/15; Y10T 428/14; Y10T 428/28; Y10T 428/2835; Y10T 428/24446;
(Continued)

(56) References Cited

U.S. PATENT DOCUMENTS 6,262,330 B1 * 7/2001 Fujisawa ................. A61L 15/58
602/41
6,503,618 B1 * 1/2003 Jakobi ..................... B26F 3/002
428/192

(Continued)

FOREIGN PATENT DOCUMENTS

GB    WO 2012028842 A1 *  3/2012    ............. A61L 15/26

*Primary Examiner* — Patricia L Nordmeyer
(74) *Attorney, Agent, or Firm* — Gerald E. Hespos; Michael J. Porco; Matthew T. Hespos

(57) ABSTRACT

An adhesive tape (1) made of silicone is intended for medical applications. The tape (1) has a sheet material (12) based on nonwoven fibers, coated on an internal face (12*a*) intended to be in contact with the skin, with a barrier membrane (14) which adheres to the sheet material, based on crosslinked silicone polymer, and with a layer (16) of atraumatic and biocompatible silicone adhesive gel, and on an external face (12*b*), with a layer (18) of a nonstick and waterproof polymer based on a fluorosilicone or fluorocarbon polymer.

12 Claims, 2 Drawing Sheets

(51) Int. Cl.
    *B32B 27/12*      (2006.01)
    *C09J 7/04*       (2006.01)
    *C09J 183/06*     (2006.01)
    *C09J 183/08*     (2006.01)
    *A61L 15/28*      (2006.01)
    *A61L 15/52*      (2006.01)
    *A61L 15/58*      (2006.01)
    *B32B 5/02*       (2006.01)
    *B32B 7/12*       (2006.01)
    *B32B 3/26*       (2006.01)
    *C08G 77/04*      (2006.01)
    *C08G 77/24*      (2006.01)

(52) U.S. Cl.
    CPC ............ *A61L 15/26* (2013.01); *A61L 15/28* (2013.01); *A61L 15/52* (2013.01); *A61L 15/58* (2013.01); *B32B 3/266* (2013.01); *B32B 5/022* (2013.01); *B32B 7/12* (2013.01); *B32B 27/12* (2013.01); *C09J 7/045* (2013.01); *C09J 183/06* (2013.01); *C09J 183/08* (2013.01); *B32B 2262/0284* (2013.01); *B32B 2262/062* (2013.01); *B32B 2307/4026* (2013.01); *B32B 2307/724* (2013.01); *B32B 2307/7265* (2013.01); *B32B 2405/00* (2013.01); *B32B 2535/00* (2013.01); *C08G 77/04* (2013.01); *C08G 77/24* (2013.01); *Y10T 428/15* (2015.01); *Y10T 428/24322* (2015.01); *Y10T 428/24446* (2015.01); *Y10T 428/2835* (2015.01); *Y10T 442/2008* (2015.04); *Y10T 442/2066* (2015.04); *Y10T 442/608* (2015.04); *Y10T 442/659* (2015.04)

(58) Field of Classification Search
    CPC ....... Y10T 428/24322; Y10T 442/2066; Y10T 442/659; Y10T 442/608; Y10T 442/2008
    See application file for complete search history.

(56) References Cited

U.S. PATENT DOCUMENTS

| | | | |
|---|---|---|---|
| 2002/0026166 A1* | 2/2002 | Graef | A61F 13/53 604/369 |
| 2007/0212520 A1* | 9/2007 | Furumori | A61F 13/0269 428/134 |
| 2009/0053441 A1* | 2/2009 | Cain | A41B 11/126 428/36.1 |

* cited by examiner

ADHESIVE TAPE MADE OF SILICONE INTENDED FOR MEDICAL APPLICATIONS

CROSS-REFERENCE TO RELATED APPLICATION

This application claims priority on U.S. Provisional Patent Appl. No. 61/725,681 filed on Nov. 13, 2012, the entire disclosure of which is incorporated herein by reference.

BACKGROUND

1. Field of the Invention

The present invention relates to unwoven tapes, in particular single-sided adhesive tapes, patches or stickers for holding medical devices, such as needles or sensors, BandAids or in particular dressings intended for the atraumatic contact of the healthy skin and of the wound.

2. Description of the Related Art

Usually, the adhesive tapes intended for the preparation of dressings and for the holding of medical devices are composed of a flat substrate, such as, for example, sheets of nonwoven, wovens, films or membranes coated on one side either with an acrylic adhesive polymer or with rubber-based formulations comprising resins, plasticizers or polymers having an instantly adhesive nature.

These compositions are generally based on polymers of high molecular weight and the adhesiveness on the skin depends on the composition and on the nature of the tackifying resins used.

These polymers having a high molecular weight confer, on the formulation, high viscosities generally of greater than several thousand mPa·s, which require a suitable process for coating the substrate with a few tens of or a few hundred g/m², which constitutes the layer generally necessary in order to obtain sufficient adhesion to the substrate and to the skin.

In order to satisfactorily coat the substrate as explained above, the formulation is generally dissolved in a solvent, or is prepared as an aqueous emulsion, and this solution is subsequently coated by conventional coating processes, for example using a scraper or rollers, before evaporating the solvent through passing through a hot air oven, in order to obtain a dry layer of appropriate formulation.

In some cases, solvent-free hot-melt polymers can be used. In this case, the coating must be carried out during the phase of melting the polymer, before cooling and solidifying the polymer layer on the substrate.

Usually, the high viscosity of the compound in solution or in emulsion or in the molten state requires adjustment of the viscosity of the liquid form in order to regulate the coating of the surface of the substrate in contact with the skin.

Furthermore, from a functional viewpoint, these polymer compositions contribute to the appearance of polymer residues adhesively bonded to the skin during the removal of the adhesive. Thus, the use of polymers/compositions of this type, this very high adhesion and the low biocompatibility (irritability, sensitivity of the skin) of these ingredients cause traumatic adhesion of the tape to the skin, in particular to delicate skin, such as that of elderly people, children, premature babies or burn victims.

Very recently, there have been developed and have appeared on the market a few "light" adhesive tapes based on PSA (Pressure-Sensitive Adhesives) silicone polymers. These compositions are based on partially or completely crosslinked silicone rubber comprising silicone resins having a high tackifying power which provide the tape with significant contact adhesion on the skin.

However, in the same way, the high viscosity of these polymers requires dissolution in a solvent in order to adjust the rheology of the liquid paste in order to coat them on a flat substrate.

Generally, the polarity of the solvents used and the low viscosity of the solution are such that the fibers of the substrate are completely impregnated and the solution can pass through them in order to exude on the external face of the substrate, which then becomes instantly adhesive and unsuitable for winding of the tape over itself and for subsequent external use on a patient.

Furthermore, the nature of the solvents used results, during their use, in high risks to the health and safety of the manufacturing personnel and to the environment, and also in high costs.

In order to prevent the tackifying composition from passing through the tape towards its external face, nonwoven suppliers or tape manufacturers have carried out the laminating, on the internal face of the nonwoven, of a membrane or of a film of polymer generally based on polyurethane or on polyolefin, before coating said membrane with the tackifying composition.

However, this operation represents a significant cost and high risks for the achievement of strong adhesion of the tackifying composition to this film.

This risk of low adhesion in its turn constitutes a high risk of delamination of the adhesive layer and of the substrate during the removal of the tape from the skin of the patient, with the disadvantages of residues and of trauma on the skin which are described above.

Thus, the solutions of the prior art are not entirely satisfactory.

One aim of the present invention is thus to solve the abovementioned problems using a solution which is simple to manufacture, relatively inexpensive, easy to use and optimized in terms of effectiveness.

SUMMARY OF THE INVENTION

Thus, a subject matter of the present invention is an adhesive tape made of silicone which is intended for medical applications, comprising a sheet material based on nonwoven fibers, coated:

on an internal face intended to be in contact with the skin, with a barrier membrane which adheres to the sheet material, based on crosslinked silicone polymer, and with a layer of atraumatic and biocompatible silicone adhesive gel, and on an external face, with a layer of a nonstick and waterproof polymer based on a fluorosilicone or fluorocarbon polymer.

The present invention thus relates to a strip of materials based on lap of nonwoven fibers exhibiting no risk of transfer of silicone gel from the internal face in contact with the skin towards the external face and providing the patient with comfort of wearing, ease of winding and unwinding, in combination with an ease of manual transverse tearing which makes it possible to cut off a piece of the desired size without an instrument.

The sheet material may be composed of one or two laps of a mixture of fibers having a low resistance to tearing and easily tearable by hand, manufactured from a mixture of short cellulose fibers and of polyethylene terephthalate fibers of medium length, bonded to one another by calendering under hot pressure and/or by a chemical bonding agent in aqueous emulsion.

The partition ratio between the fibers preferably varies from 10 to 40% of PET for 90 to 60% of cellulose, the weight of the nonwoven lap varies from of the order of 30 to 70 g/m² for a thickness of 0.10 à 0.30 mm, the cellulose fibers exhibit a length of the order of 1 mm to 20 mm and the PET fibers exhibit cylindrical fiber structures with a linear density of between 0.1 dtex and 5 dtex, and with a length of the order of 2 mm to 20 mm.

The nonwoven lap may exhibit a surface structure comprising small folds of material in profusion in the transverse direction, so as to confer on the material properties of deformation under low elongation stress in the longitudinal direction.

The tape also may comprise a layer of an adhesive crosslinked silicone gel, atraumatic and biocompatible for the skin, which adheres by a copolymerization reaction to a membrane made of crosslinked silicone forming a barrier on the internal face of the nonwoven lap.

The tape additionally may comprise a thin continuous barrier membrane or a noncontinuous layer made of crosslinked silicone polymer laminated to the fibers of the internal face of the nonwoven lap. The role of this membrane is to form an adhesion primer of strong adhesion to the fibers and to the atraumatic silicone gel which will subsequently be coated above, to form a barrier layer in order to prevent the adhesive silicone gel from diffusing through the fibers and to form a chemical barrier between the silicone gel and the components of the nonwoven which are liable to be inhibitors of the polymerization reaction of the gel based on platinum catalyst.

The tape preferably is perforated with small orifices, so as to provide it with high permeability to the vapor resulting from the exudation of the skin and in order to prevent maceration of wet skin.

The sheet of nonwoven fibers preferably is perforated with orifices with a diameter of 0.05 to 0.5 mm, so as to provide the final material with an appearance of a woven or knitted textile structure, to improve the permeability to water vapor resulting from the exudation of the skin, to improve the tearability, and/or to provide the external surface of the material with properties of low friction and of high comfort of wearing, on contact with any textile or item of clothing, and/or to provide, for the patient, great comfort of wearing, on contact with a region of the skin capable of deforming, of folding, or of comprising hollow regions and regions possessing relief.

The edges of the tape preferably are cut over their entire length according to a repeating geometrical design, such as triangular teeth, half-disks, or random indentations, in order to provide the tape with an ease of transverse manual tearing.

The permeability of the water vapor of the layer of the adhesive silicone gel is preferably between approximately 500 and 2000 g/m²/24 h, measured with water according to the inverted cup method (standard EN 13 726-2), and preferably approximately 1000 g/m²/24 h.

The nonwoven fibers may be dyed, and/or the chemical agent for bonding the fibers is pigmented and coated with a barrier layer of crosslinked silicone and with a layer of an adhesive of crosslinked silicone gel in which the silicone polymers are pigmented.

The invention will now be described in more detail with reference to specific embodiments given purely by way of illustration and represented in the appended figures.

DETAILED DESCRIPTION OF THE PREFERRED EMBODIMENTS

Figure 1:
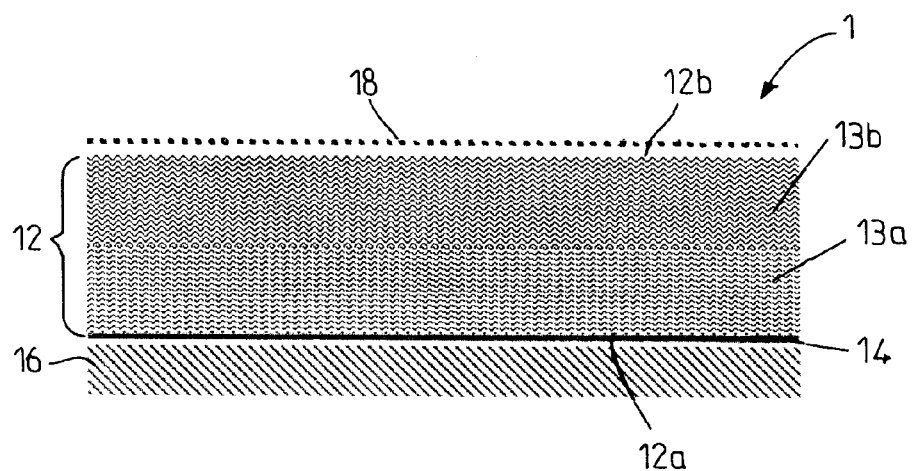
FIG. 1 is a sectional view of an adhesive tape in accordance with the present invention.
Figure 2:
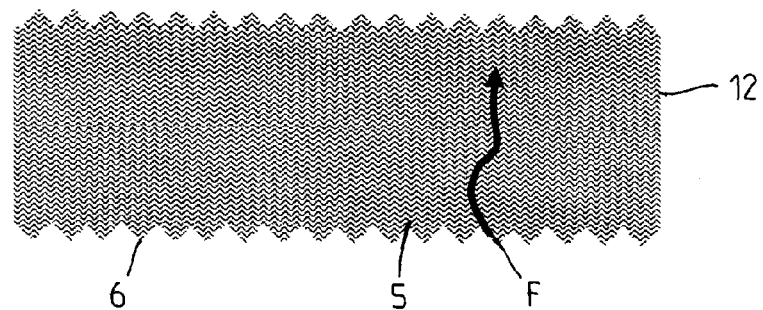
FIGS. 2 to 4 are top views of an easily tearable sheet based on nonwoven fibers belonging to the adhesive tape.

FIG. 1 represents an adhesive tape 1 intended for medical applications, for example for the purpose of preparing a dressing, comprising a sheet material 12 based on nonwoven fibers.

The sheet material 12 is coated on an internal face 12a, intended to be in contact with the skin, with a barrier membrane 14 which adheres to the sheet material, based on crosslinked silicone polymer, and with an external layer 16 of atraumatic and biocompatible adhesive silicone gel.

The sheet material 12 is also coated, on an external face 12b, with a layer 18 of a nonstick and waterproof polymer based on a fluorosilicone or fluorocarbon polymer. This nonstick coating 18 constitutes the external face of the tape 1 and exhibits a waterproof behavior in order to prevent the nonwoven lap from becoming wet when the patient comes into contact with water. Finally, it makes it possible to prevent the tape, wound in the form of a small roll, from adhering to itself.

The nonwoven lap 12 is composed of a continuous structure of fibers, either in a homogeneous layer or in two homogeneous layers of interpenetrated fibers, as is illustrated.

In the second case, the layers confer, on the two faces of the nonwoven lap 12 and thus on the final tape 1, highly distinct functional properties.

In particular, the external face 12b is composed of dense and shorter fibers, in order to confer thereon properties of flatness, of softness and of nonstickiness. The internal face 12a is composed, for its part, of longer and less densified fibers with a rougher surface structure necessary for mechanical anchoring and for significant wetting of the fibers during the coating with the silicone polymer forming the internal silicone membrane.

The nonwoven lap 12 is manufactured, for example, according to an aqueous process by the papermaking route known as wet laid process. The fibers are composed of a homogeneous mixture of short cellulose fibers and of medium-length fibers of polyethylene terephthalate (PET).

The cellulose fibers confer, on the lap 12, the bulking and flatness properties necessary for uniform coating, in combination with low mechanical resistance to tearing for easy tearing of the tape 1 by hand.

For their part, the polyethylene terephthalate fibers confer, on the lap 12, sufficient mechanical properties both for maintenance of the lap 12 during the process of coating and of cutting tape 1 and for the handling of said tape 1, for example by a nurse, without the risk of breaking. These polyethylene terephthalate fibers also make possible good mechanical strength of the lap 12 in the wet state, and also good mechanical protection of the patient against any risk of perforation or of abrasion.

The cellulose and PET fibers are generally chemically bonded to one another using a chemical bonding agent in the aqueous phase, or else by partial hot melting using hot rollers under pressure. The chemical bonding agent is typically based on polymers in emulsion commonly used in the papermaking industry.

Advantageously, the distribution ratio between the fibers varies from 10 to 40% of PET for 90 to 60% of cellulose. A typical weight range for nonwoven lap 12 varies from of the order of 30 to 70 g/m² for a thickness of 0.10 to 0.30 mm. The cellulose fibers exhibit fibers with a length of the order of 1 mm to 20 mm, while the PET fibers exhibit a cylindrical structure with a linear density of between approximately 0.1 dtex and 5 dtex and with a length of the order of 2 mm to 20 mm.

The fibers are typically distributed in a homogeneous single layer. For this innovation, there has been developed a lap formed of two layers 13a and 13b of two specific densities of fibers which provide the final product with noteworthy functional properties.

The external layer 13b is composed of a high density of fibers. The resulting functions are a good leaktightness to the liquid silicone prepolymer forming the membrane, during the process of coating with this membrane, which makes it possible to prevent transfer of this liquid polymer towards the external face 12b of the lap 12. In addition, this confers, on the external face 12b of the lap 12 and thus of the final tape 1, a very soft feel of velvety type on contact with the patient or with an item of clothing which covers the skin.

In order to further increase this velvety aspect, there is carried out, at the end of the manufacture of the lap 12, an operation of coating the external face 12b using a nonstick polymer, the functionality of which is to form the layer 18 which makes it possible to prevent the adhesive silicone gel of the internal face 12a from adhesively bonding to the external face 12b when the tape 1 is wound/unwound, in combination with properties of low wetting when the dressing comes into contact with water, for example during a shower or washing of the patient.

Typically, the nonstick agents used against the adhesive bonding of the adhesive silicone gel and against the wetting by water are of the polyfluorocarbon or fluorosilicone polymer type, presented in aqueous emulsion. They are deposited on the external face 12b of the lap 12 by any type of coating process typically encountered in the textile or papermaking industry, for example using rollers or by padding.

During the operation of drying from the water of the emulsion, a hot calendering using a mirror-finished metal roller can further improve the surface appearance.

The interior layer 13a is for its part composed of a mixture of fibers having a lower density, so as to provide the internal surface 12a with a rougher surface, intended to offer greater contact and a better mechanical anchoring of the silicon polymer, in combination with better chemical bonding between the silicone and the fibers, in particular the PET fibers.

The layers 13a and 13b are manufactured together starting from one and the same fiber dispersion pulp, comprising the chemical agent for bonding the fibers, with the possibility of varying the concentration of pulp during a wet deposition process immediately before the draining of the pulp and the application of hot drying rollers of this pulp layer and then drying by hot air of the lap of fibers thus obtained.

The agent for chemical bonding of the fibers must be judiciously chosen so as not to negatively interfere with the platinum-catalysis polymerization of the polymer forming the interior silicone membrane. Typically, an emulsion of acrylate polymers, of polyvinyl alcohol, of polyamide or of polyester can be chosen.

Figure 5:
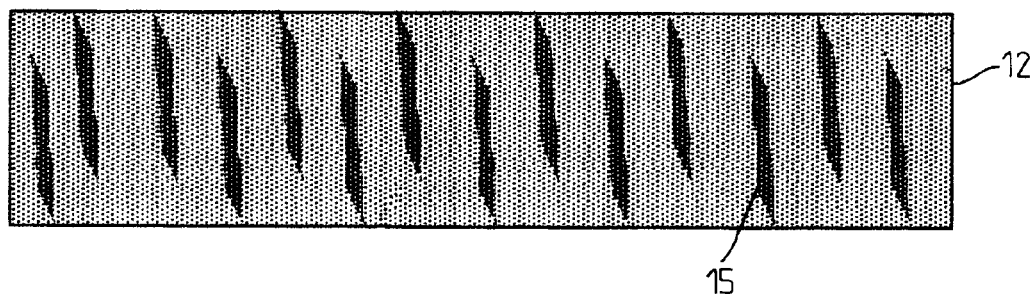
FIG. 5 is a top view of an alternative embodiment of FIGS. 2 to 4.
Figure 6:
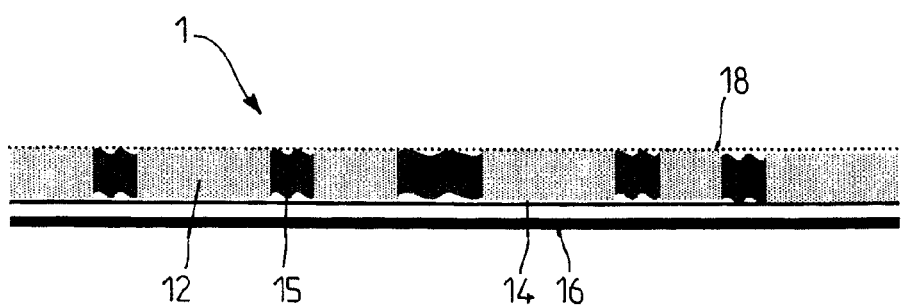
FIG. 6 is a sectional view of an adhesive tape in accordance with the alternative embodiment of FIG. 5.

Such a nonwoven lap 12 thus exhibits a flat surface, the fibers of which are contiguous and the elongation under deformation stress of which is low. This type of structure exhibits the disadvantage of being poorly suited to attachment to parts of the body subjected to great deformation, such as in the folds or the joints. In order to improve the comfort of positioning and of wearing by the patient, and in order to increase the security of attachment to the skin, there has been developed an adhesive gel tape on the base of a nonwoven lap 12 of fibers such as described above, which receives, after manufacture of the lap, an additional operation of transverse crumpling and of longitudinal forcing of the material into small transverse folds 15 giving a "crepe paper" appearance, as illustrated in FIGS. 5 and 6.

This operation of longitudinal structuring of the nonwoven lap 12, which results in overfeeding of the material, makes it possible to obtain properties of longitudinal deformation of the lap which provide it with a good ability to deform under stress. Thus, the elongation under load of this structure is of the order of 10% under a load of 1 N/cm and the elongation before breaking is 20%, against 10% for a nonwoven lap devoid of crimping.

This operation is carried out dynamically by overfeeding a length of lap across a first rotating roller on which is positioned a metal scraper which will pinch the forwardly progressing lap. As it is not possible for the excess of material overfed by the first roller to pass between the scraper, a second roller creates small transverse folds 15 forming a store of length for greater elongations under stress, as explained above.

It is also important to prevent the adhesive silicone gel 16 from passing through the layer of fibers 12 when a pressure is applied to the tape by the nurse or by the patient, during the positioning of the dressing or of the device, or else prior to the positioning by application of pressure during the cutting and the winding of the roll of tape.

Furthermore, it is also important to prevent any delamination of the adhesive gel 16 when the tape 1 is removed from the skin by tearing off.

In order to arrive at this result, it is advisable, to this end, to obtain a strong adhesion between the adhesive silicone gel 16 and the lap of unwoven 12. Thus, a simple mechanical anchoring of the layer of silicone gel 16 to the fibers 12 does not provide the patient with sufficient security and it is necessary to improve the mechanical adhesion by an adhesion of chemical nature between the layer of the adhesive silicone gel 16 and the layer of fibers 12.

The present innovation consists in generating a continuous intermediate membrane 14 made of a chemically reactive silicone polymer, so as to create a barrier membrane to the passage of adhesive gel 16 through the fibers 12 and to create a strong mechanical and chemical adhesion between the fibers 12, on the one hand, and the layer of adhesive gel 16 on the other hand, in order to prevent the gel from passing through the fibers and to prevent tearing from taking place and material residues from occurring when the tape is removed from the skin.

The intermediate membrane 14 is composed of a mixture of prepolymers which are linear or partially branched or with a three-dimensional structure of resin type, having a high molecular weight, of alkenyl- or vinylsilicone type, formulated with a chemical bonding agent of organosilane type and a catalytic system typically based on alkyl orthotitanate and platinum derivatives. The reactive formulation is produced inline via continuous pumping, metering and dynamic or static mixing equipment, and thus to feed the coating line continuously. The typical products used for this application can be Silbione HC2 2512 from Blue Star Silicone or equivalent.

The coating line is composed of a device of roller and scraper type for laminating a liquid film on a metal roller, followed by a system for transferring the liquid film onto the internal face 12a of the lap of fibers 12 of the reverse roll type, either in corotation or in counterrotation, or roller in the air.

Subsequently, the nonwoven lap 12 coated with the liquid film of prepolymers and of the catalytic system is transferred continuously through a hot air oven in order to activate the polymerization by a polyaddition reaction of the prepolymers, to obtain, at the oven outlet, a solid layer of polymerized silicone forming a continuous membrane 14 and, in related fashion, a chemical bonding between the polyethylene terephthalate fibers 12 and the silicone polymer forming the membrane 14 which will generate the strong adhesion between the adhesive silicone gel 16 coated in a second stage and the lap of fibers of the nonwoven 12.

The typical weights deposited for the composition of this barrier membrane 14 are from 10 to 70 $g/m^2$, depending on the structure and on the surface area of the internal face 12a of the nonwoven lap 12.

The layer of adhesive silicone gel 16 produced in a second step on the internal face 12a of the nonwoven lap 12 is composed of a mixture of silicone prepolymers of alkenyl- or vinylsilicone type of low molecular weight necessary for the attainment of a crosslinked structure of "gel" type, mixed with prepolymers of hydrosiloxane type, and of a catalysis system based on platinum and of regulators of polymerization kinetics of polyol type, so as to obtain a final mixture, the pot life of which is compatible with the continuous feeding of the line for coating with the gel layer, and liable to create copolymerization with the first layer constituting the barrier membrane 14.

The type of silicone used is a crosslinked silicone gel polymer comprising atraumatic properties, complete biocompatibility in contact with the skin and the wound, coated on a silicone membrane 14 strongly adhered to the internal face 12a of the fibers of the nonwoven lap 12.

The weights of silicone deposited for this layer of adhesive gel 16 are typically within a range from 50 to 200 $g/m^2$, according to the level of adhesion desired on the skin for the adhesive tape.

The silicone products conventionally used for this deposition can be Silbione HO 2 2030 from Blue Star Silicone or its equivalent.

The permeability to water vapor of this material can range from 500 to 2000 $g/m^2/24$ h, measured with water according to the inverted cup method, which is a level of permeability regarded as sufficient on healthy skin for preventing the phenomena of maceration in a closed environment due to exudation.

A layer of noncontinuous coating can also be produced by a different coating technology, in particular flexographic printing by rollers, use of continuous flow nozzles, of rollers having a perforated metal screen or else by transfer roller. The diameter of the noncoated surfaces will be small, of the order of 0.1 to 0.5 mm, so as to retain a sufficient adhesive strength of the gel on the skin. Such a noncontinuous coating layer 16 is advantageous in increasing the permeability to vapor resulting from exudation of the skin through the tape to permeability levels greater than 1000 $g/m^2/24$ h and thus preventing any risk of maceration of the skin in the event of a strongly exuding wound.

It is also possible to obtain a colored presentation of adhesive tape 1 using different methods.

According to a first technique for pigmenting the barrier silicone layer 14 or the silicone gel layer 16, use is made of a predispersion of pigment in a reactive oil based on reactive silicone prepolymer which will be copolymerized at the same time as the silicone prepolymers forming the barrier layer 14 or the gel layer 16.

According to another technique for dyeing the fibers of the nonwoven lap, use is made of conventional processes for dyeing textile fibers in the body or the pigmentation of the binding polymer for the fibers introduced into the aqueous pulp of fibers during the manufacture of the nonwoven lap 12.

Very obviously, the manufacturing process described above will also be used for the coating of a textile-based support intended to produce silicone adhesive gel tapes.

After polymerization of the layer of adhesive silicone gel 16, the sheet of the material thus manufactured will be wound over itself, one face over the other, in order to be cut into a roll of tape with a final width for the final use.

Figure 4:
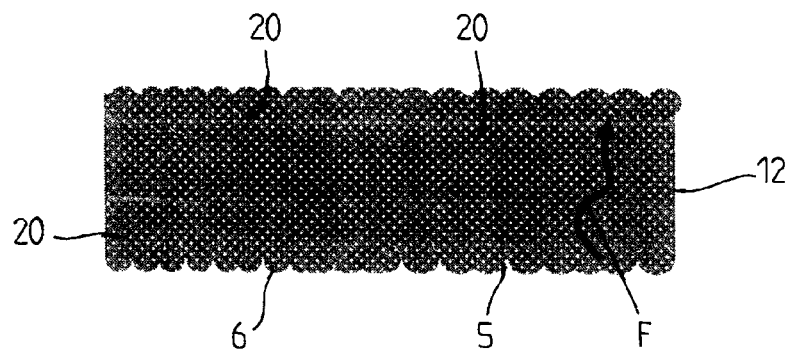

Before winding, the surface of the material can be perforated using a hot needle cylinder or else using a cutting punch-roller under pressure, so as to create small perforations 20 (FIG. 4) with a diameter of 0.05 to 0.5 mm, so as to obtain a perforated structure of very high permeability to vapor of greater than 2000 $g/m^2/24$ h, or else in order to form the base of a material for a dressing which allows the liquid exudates from the wound to pass through, which exudation will subsequently be absorbed on the upper face by an absorbent material.

Figure 3:
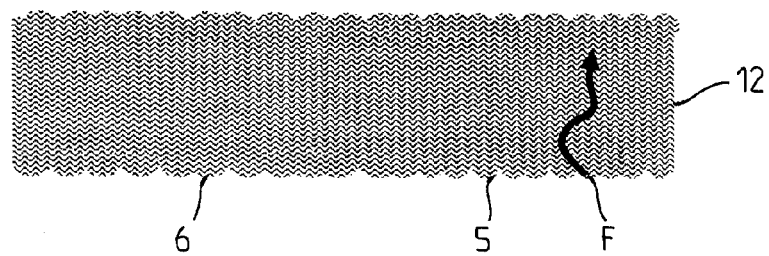

As is illustrated in FIGS. 3 and 5, the edges 5 of the tape 1 wound into a roll can also be provided with small notches 6 having a diamond or half-disk shape periodically cut out in the length, so as to create tearing stress concentrations. Thus, the propagation of the transverse tear F of the tape 1 will facilitate the manual cutting of a piece of tape by the final user (patient, medical personnel).

It is obvious that the detailed description of the subject matter of the invention, given solely by way of illustration, does not in any way constitute a limitation, the technical equivalents being also included within the field of the present invention.

What is claimed is:

1. An adhesive tape (1) for medical applications, comprising:
a nonwoven sheet material (12) having an internal face (12a) and an external face (12b), the nonwoven sheet material comprising an internal layer (13a) that carries the internal face (12a) and an external layer (13b) that carries the external face (12b), the external layer (13b) having a density greater than a density of the internal layer (13a),
the internal face carrying a barrier membrane (14) which adheres to the sheet material, the barrier membrane comprising a crosslinked silicone polymer, the barrier membrane carrying an atraumatic and biocompatible silicone adhesive gel layer (16),
the external face (12b) carrying a nonstick and waterproof polymer layer (18) comprising a fluorosilicone or fluorocarbon polymer;
wherein the sheet material (12) includes a profusion of small folds (15) in a transverse direction, thereby providing a capacity for elongation under low stress in the longitudinal direction.

2. An adhesive tape (1) for medical applications, comprising:

a nonwoven sheet material (12) having an internal face (12a) and an external face (12b), the nonwoven sheet material comprising an internal layer (13a) that carries the internal face (12a) and an external layer (13b) that carries the external face (12b), the external layer (13b) having a density greater than a density of the internal layer (13a), the internal face carrying a barrier membrane (14) which adheres to the sheet material, the barrier membrane comprising a crosslinked silicone polymer, the barrier membrane carrying an atraumatic and biocompatible silicone adhesive gel layer (16), the external face (12b) carrying a nonstick and waterproof polymer layer (18) comprising a fluorosilicone or fluorocarbon polymer.

3. The tape of claim 2, wherein the sheet material (12) is composed of a mixture of fibers and having a low resistance to tearing and easily tearable by hand, wherein the sheet material includes a mixture of short cellulose fibers and of medium length polyethylene terephthalate (PET) fibers bonded to one another by calendering under hot pressure and/or by a chemical bonding agent.

4. The tape of claim 3, wherein the sheet material includes a ratio of 10 to 40% of PET for 90 to 60% of cellulose, wherein the sheet material has a weight of 30 to 70 g/m$^2$ and a thickness of 0.10 to 0.30 mm, wherein the cellulose fibers have a length of the order of 1 mm to 20 mm, and the PET fibers exhibit cylindrical fiber structures with a linear density of between 0.1 dtex and 5 dtex, and with a length of the order of 2 mm to 20 mm.

5. The tape of claim 2, wherein the tape is perforated with small orifices (20) to provide high permeability to vapor resulting from the exudation of the skin and to prevent maceration of wet skin.

6. The tape of claim 2, wherein the sheet of nonwoven fibers is perforated with orifices (20) with a diameter of 0.05 to 0.5 mm, so as to provide the final material with an appearance of a woven or knitted textile structure, in order to improve the permeability to water vapor resulting from the exudation of the skin, to improve the tearability, and/or to provide the external surface of the material with properties of low friction and of high comfort of wearing, on contact with any textile or item of clothing, and/or in order to provide, for the patient, great comfort of wearing, on contact with a region of the skin capable of deforming, of folding, or of comprising hollow regions and regions possessing relief.

7. The tape of claim 2, wherein edges (5) of the tape are cut over their entire length according to a repeating geometrical design (6) to provide the tape (1) with an ease of transverse manual tearing (F).

8. The tape of claim 2, wherein permeability of the water vapor of the layer of the adhesive silicone gel (16) is between approximately 500 and 2000 g/m$^2$/24 h, measured with water according to the inverted cup method (standard EN 13 726-2).

9. The tape of claim 2, wherein the nonwoven fibers (12) are dyed, and/or the chemical agent for bonding the fibers is pigmented and coated with a barrier layer of crosslinked silicone and with a layer of an adhesive of crosslinked silicone gel in which the silicone polymers are pigmented.

10. An adhesive tape (1) for medical applications, comprising:

a nonwoven sheet material (12) having an internal face (12a) and an external face (12b), the nonwoven sheet material comprising an internal layer (13a) that carries the internal face (12a) and an external layer (13b) that carries the external face (12b), the external layer (13b) having a density greater than a density of the internal layer (13a), the internal face carrying a barrier membrane (14) which adheres to the sheet material, the barrier membrane comprising a crosslinked silicone polymer, the barrier membrane carrying an atraumatic and biocompatible silicone adhesive gel layer (16), the external face (12b) carrying a nonstick and waterproof polymer layer (18) comprising a fluorosilicone or fluorocarbon polymer;

wherein the sheet material (12) is composed of a mixture of fibers and having a low resistance to tearing and easily tearable by hand, wherein the sheet material includes a mixture of short cellulose fibers and of medium length polyethylene terephthalate (PET) fibers bonded to one another by calendering under hot pressure and/or by a chemical bonding agent, wherein the sheet material includes a ratio of 10 to 40% of PET for 90 to 60% of cellulose, wherein the sheet material has a weight of 30 to 70 g/m$^2$ and a thickness of 0.10 to 0.30 mm, wherein the cellulose fibers have a length of the order of 1 mm to 20 mm, and the PET fibers exhibit cylindrical fiber structures with a linear density of between 0.1 dtex and 5 dtex, and with a length of the order of 2 mm to 20 mm; and wherein the sheet material (12) includes a profusion of small folds (15) in a transverse direction, thereby providing a low elongation stress in the longitudinal direction.

11. The tape of claim 10, wherein the barrier membrane is a thin continuous barrier membrane or a noncontinuous barrier membrane, and wherein the barrier membrane is made of crosslinked silicone polymer (14) laminated to the fibers of the internal face (12a).

12. The tape of claim 11, wherein the atraumatic and biocompatible silicone adhesive gel layer (16) is adhered by a copolymerization reaction to the barrier membrane.

* * * * *